US011931120B2

(12) United States Patent
Liang et al.

(10) Patent No.: US 11,931,120 B2
(45) Date of Patent: Mar. 19, 2024

(54) TARGETED SEED IMPLANTING ROBOT SUITABLE FOR CLINICAL TREATMENT OF A HUMAN PATIENT IN THE LITHOTOMY POSITION

(71) Applicants: ANHUI POLYTECHNIC UNIVERSITY, Wuhu (CN); WUHU ANPU INSTITUTE OF TECHNOLOGY ROBOTICS INDUSTRY CO., LTD., Wuhu (CN)

(72) Inventors: Yi Liang, Wuhu (CN); Buyun Wang, Wuhu (CN); Dezhang Xu, Wuhu (CN); Benchi Jiang, Wuhu (CN)

(73) Assignees: ANHUI POLYTECHNIC UNIVERSITY, Wuhu (CN); WUHU ANPU INSTITUTE OF TECHNOLOGY ROBOTICS INDUSTRY CO., LTD., Wuhu (CN)

( * ) Notice: Subject to any disclaimer, the term of this patent is extended or adjusted under 35 U.S.C. 154(b) by 499 days.

(21) Appl. No.: 17/275,668

(22) PCT Filed: Jul. 10, 2020

(86) PCT No.: PCT/CN2020/101284
§ 371 (c)(1),
(2) Date: Mar. 11, 2021

(87) PCT Pub. No.: WO2021/022971
PCT Pub. Date: Feb. 11, 2021

(65) Prior Publication Data
US 2022/0039884 A1 Feb. 10, 2022

(30) Foreign Application Priority Data
Aug. 3, 2019 (CN) .......................... 201910714054.7

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/76* (2016.02); *A61B 34/77* (2016.02); *A61N 5/1007* (2013.01); *B25J 9/1035* (2013.01)

(58) Field of Classification Search
CPC ......... A61B 34/30; A61B 34/76; A61B 34/77; A61B 2090/064; A61B 2090/066;
(Continued)

(56) References Cited

U.S. PATENT DOCUMENTS 6,582,354 B2    6/2003   Ellard
2008/0004481 A1*  1/2008  Bax ................... A61B 17/3403
                                                600/7
(Continued)

FOREIGN PATENT DOCUMENTS

CN    105268093 A    1/2016
CN    105534597 A    5/2016
(Continued)

OTHER PUBLICATIONS

"Salcudean, et al., A Robotic Needle Guide for Prostate Brachytherapy, 2008, 2008 IEEE International Conference on Robotics and Automation" (Year: 2008).*

(Continued)

*Primary Examiner* — Joseph M Dietrich
*Assistant Examiner* — Michael T. Holtzclaw
(74) *Attorney, Agent, or Firm* — Zhu Lehnhoff LLP

(57) ABSTRACT

A targeted seed implanting robot suitable for clinical treatment of a human patient in the lithotomy position includes a rack, and further includes a position and posture adjusting mechanism, a contact force feedback friction wheel type targeted seed implanting mechanism, and a sine elastic amplification moment compensation mechanism; and the specific use steps are as follows: S1, driving; S2, meshing; S3, swing; S4, transverse movement; S5, compensation moment; S6, linear motion; S7, rotary motion; S8, detection; and S9, transmission of information.

7 Claims, 3 Drawing Sheets

(51) Int. Cl.
*A61N 5/10* (2006.01)
*B25J 9/10* (2006.01)

(58) Field of Classification Search
CPC ... A61N 5/1007; A61N 5/1001; B25J 9/1035; B25J 19/0016
See application file for complete search history.

(56) References Cited

U.S. PATENT DOCUMENTS

| | | | |
|---|---|---|---|
| 2010/0036245 A1* | 2/2010 | Yu | A61N 5/1027 600/7 |
| 2012/0265051 A1* | 10/2012 | Fischer | A61B 34/30 73/800 |
| 2019/0090966 A1 | 3/2019 | Kang et al. | |
| 2022/0184416 A1* | 6/2022 | Flynn | A61N 5/1002 |

FOREIGN PATENT DOCUMENTS

| | | |
|---|---|---|
| CN | 105727431 A | 7/2016 |
| CN | 107320195 A | 11/2017 |
| CN | 109499009 A | 3/2019 |
| CN | 110404157 A | 11/2019 |
| CN | 110496301 A | 11/2019 |

OTHER PUBLICATIONS

"Zhang, et al., Semi-automated Needling and Seed Delivery Device for Prostate Brachytherapy, 2006, 2006 IEEE/RSJ International Conference on Intelligent Robots and Systems" (Year: 2006).*
Search Report, issued by CNIPA, in CN2019107140547, dated Mar. 31, 2021.
First Office Action (OA1), issued by CNIPA, in CN2019107140547, dated Apr. 9, 2021.
Research on Key Technology of Prostate Radioactive Seed Implantation Robot, by Yi Liang, dated Feb. 28, 2018.
Office Action (rejection), issued by CNIPA, in CN2019107140547 (priority application), dated Jan. 6, 2022.
International Search Report issued by CNIPA as the searching authority in PCT/CN2020/101284, dated Sep. 28, 2020.
Written Opinion issued by CNIPA as the searching authority in PCT/CN2020/101284, dated Sep. 28, 2020.

* cited by examiner

TARGETED SEED IMPLANTING ROBOT SUITABLE FOR CLINICAL TREATMENT OF A HUMAN PATIENT IN THE LITHOTOMY POSITION

FIELD OF THE DISCLOSURE

The present disclosure relates to the technical field of medical equipment, in particular, to a targeted seed implanting robot suitable for clinical treatment of a human patient in the lithotomy position.

BACKGROUND OF THE DISCLOSURE

According to the 2018 Cancer Report, China has 4.29 million new cancer cases, accounting for 20% of the world, and 2.81 million deaths each year. Brachytherapy is suitable for treatment of urogenital system tumors, abdominal tumors, digestive system tumors and intracranial tumors. Clinically, in this type of surgery, using the gland cavity as the surgical approach, a doctor handholds a seed implanting instrument through a guide template to epidermis, using the epidermis as an entrance to puncture the gland dura and finally reach the tumor gland target area for local precise radiation. Through a large number of clinical surgical evaluations, advantages of this type of surgery have been confirmed, including strong targeting, less trauma, fast curative effect, and fewer side effects, etc. At present, most of the seed implantation at home and abroad is performed manually. During the operation, the doctor needs to repeatedly adjust the path from the puncture entrance to the target point, and he/she must maintain complete hand-eye consistency and continuous force control throughout the puncture to ensure the seeds are placed in the desired position. Manual brachytherapy suffers from the following problems: on the one hand, in order to ensure quality of the surgery, doctors must adjust the path from the percutaneous puncture point to the target point, and thus they are subject to decrease of hand sensitivity due to long-time fatigue operation since generally hundreds of seeds have to be implanted to tumor patients, making it difficult to guarantee the accuracy of ≤2 mm. On the other hand, fatigue of hands and eyes caused by long-time surgical operations makes it difficult to achieve precise treatment of malignant tumors, and there is a lack of treatment methods with certain autonomous capabilities.

The successful application of the Da Vinci surgical robot shows that the surgical robot is superior to the surgeon's bare-handed operation in terms of operation accuracy, reliability and body damage reduction.

Targeted seed implanting robots at home and abroad began in the early $21^{st}$ century. The University of Rochester in the United States has developed a rectangular coordinate seed implanting robot, which, using movable joints to form a rectangular coordinate cantilever structure, would reduce the overall stiffness, occupy more space and is poor in moving response ability. Cluj Napoca University of Technology in Romania has developed an CRRU+CRU modular parallel seed implanting robot, having a problem of working singularities during control. Tianjin University has designed a hybrid parallel seed implanting robot having its structure and materials suitable for nuclear magnetic compatible environment, whereas the overall structure thereof is too complicated, and it is difficult to make control. Generally, a cantilever articulated robot is more suitable for operation in a narrow space with respect to a human patient in the lithotomy position, but when the cantilever articulated configuration is operated at low speed with high precision, time-varying gravitational moment will cause large driving torque fluctuations, which deteriorates stable performance of the robot at low speed. In addition, when the robot controls positioning of an interventional device in a soft tissue, the robot completely lacks real-time touch force perception in the case of encountering blood vessels, arteries, and bones in the process of puncture, and thus using a fixed procedure for the puncture will inevitably cause serious medical accidents. Therefore, it is theoretically valuable and practically significant to provide a targeted seed implanting robot with stable driving process and high implantation accuracy, having a touch force sensing device, and suitable for air operations in a narrow space with respect to a human patient in the lithotomy position.

SUMMARY OF THE DISCLOSURE

In order to solve the above problems, the present disclosure provides a targeted seed implanting robot suitable for clinical treatment of a human patient in the lithotomy position.

A targeted seed implantation robot suitable for clinical treatment of a human patient in the lithotomy position, including a rack, and also including:
- a position and posture adjustment mechanism provided on the rack to realize transmission of movement and forces under dynamic conditions;
- a contact force feedback friction wheel type targeted seed implanting mechanism provided on the position and posture adjustment mechanism to cooperate with a user to improve force information perception ability in the targeted seed implanting process; and
- a sine elastic amplification moment compensation mechanism provided on the rack and cooperating with the position and posture adjustment mechanism to amplify an elastic force through a sinusoidal force for torque compensation.

The position and posture adjustment mechanism includes a big arm, a big arm reduction motor connected with the big arm, a driving gear arranged on the big arm, a small arm arranged on the big arm, a wrist connected with the small arm through a hinge, and a connecting flange connected at the wrist.

The contact force feedback friction wheel type targeted seed implanting mechanism includes an external pin driving mechanism and a friction wheel type internal pin driving mechanism cooperating with the connecting flange, a seed loading transition device cooperating with the friction wheel type internal pin driving mechanism, and a contact force feedback external pin cooperating with the seed loading transition device.

The friction wheel type internal pin driving mechanism includes a sliding table arranged on an external pin driving mechanism, a bottom plate arranged on the sliding table, an internal pin arranged on the bottom plate, the internal pin cooperating with the friction wheel for transmission.

The seed loading transition device is a seed implanting channel, the contact force feedback type external pin is a hollow multidimensional force sensor, and the external pin and the multidimensional force sensor cooperate for injection.

The sine elastic amplification moment compensation mechanism includes a driven gear meshing with the driving gear, a crank slider mechanism cooperating with the driven gear, and an elastic amplification mechanism that cooperates with the crank slider mechanism to achieve elastic force amplification and compensation.

The crank slider mechanism includes a crank and a connecting rod cooperating with the crank; the elastic amplification mechanism includes a lower sliding rack cooperating with the connecting rod, a linear slide rail provided on the lower sliding rack, a pinion gear meshing with the lower sliding rack, a large gear cooperating with the pinion gear, an upper sliding rack that cooperates with the large gear through a rack and pinion pair, a slider provided on the upper sliding rack, a linear guide rod that cooperates with the slider, and several sets of compression springs provided on the linear guide rod.

A method suitable for clinical use of a targeted seed implanting robot on a human patient in the lithotomy position, having specific steps as follows:

S1: Driving: driving the big arm reduction motor to cause motion of the driving gear and the big arm;

S2: Meshing: meshing the driving gear with the driven gear;

S3: Swing: the driven gear, through cooperation with the crank, is connected to the connecting rod via a revolute pair, and the driving gear is rotated to cause rotation of the crank, the crank causes swing of the connecting rod via the revolute pair, and a distal end of the connecting rod drives the upper sliding rack to move;

S4: Transverse movement: the lower sliding rack, when moving horizontally in a transverse direction, drives the upper sliding rack to move horizontally in an opposite direction;

S5: Compensation moment:

a: The upper sliding rack is moved to compresses the several sets of compression springs, elastic force of the compression springs being amplified by the pinion gear and the large gear cooperating with the pinion gear; and b: The amplified elastic force reacts on the upper sliding rack, and moment is transmitted through the big arm and the small arm to the contact force feedback friction wheel type targeted seed implanting mechanism;

S6: Linear motion: When the external pin drive mechanism is moving, it drives the external pin to move in a straight line, achieving precise positioning of the external pin by controlling a moving distance of the sliding table;

S7: Rotary motion: When the external pin reaches a designated position, the friction wheel type internal pin driving mechanism drives two sets of friction wheels arranged symmetrically to rotate, and the internal pin reciprocating in and out of the seed implanting channel under the action of rolling friction forces provided by the friction wheels and reciprocating into the seed loading transition device;

S8: Detection: After entering the hollow multidimensional force sensor fixedly connected to the contact force feedback external pin, the hollowed external pin reaches the designated position, and the hollow multidimensional force sensor measures forces and moments received by the external pin in real time when the external pin is moving;

S9: Transmission of information: The force information is transmitted to a controller, which controls motion state of the external pin driving mechanism and the friction wheel type internal pin driving mechanism according to the force information, and performs seed implantation.

The present disclosure brings about the following beneficial effects: use of a sine elastic amplification moment compensation mechanism can realize compensation of lower weight moment of any position shape of a big arm, reduce fluctuation of driving moment, improve stability of tail-end low-speed operation of the robot, and, based on the position and posture adjusting mechanism, make it possible to adjust an incidence angle of the external pin of the implanting mechanism in a fixed-point mode when it enters into an epidermal incident point, which could plan a pin entrance path more flexibly, and, in addition, the contact force feedback friction wheel type targeted seed implanting mechanism installed at the tail end of the position and posture adjusting mechanism improves the force information perception ability in the targeted seed implanting process.

BRIEF DESCRIPTION OF THE DRAWINGS

The present disclosure will be further described below with reference to the drawings and embodiments.

FIG. 4 is a three-dimensional schematic diagram of the contact force feedback friction wheel type targeted seed implanting mechanism of the present disclosure;

DETAILED DESCRIPTION OF THE EMBODIMENT(S) OF THE DISCLOSURE

Figure 1:
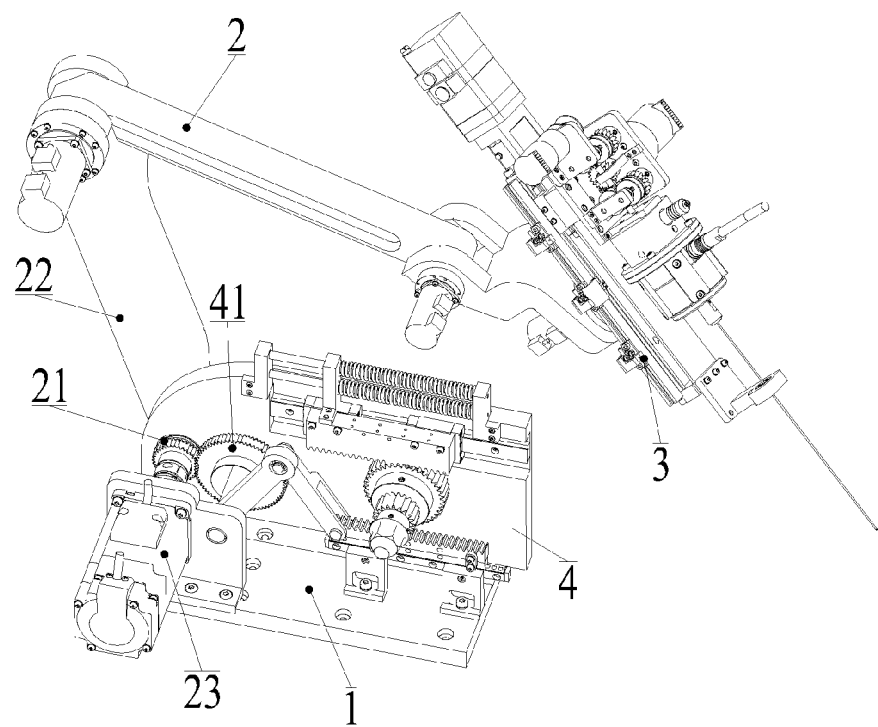
FIG. 1 is a schematic diagram of the three-dimensional structure of the present disclosure.
Figure 2:
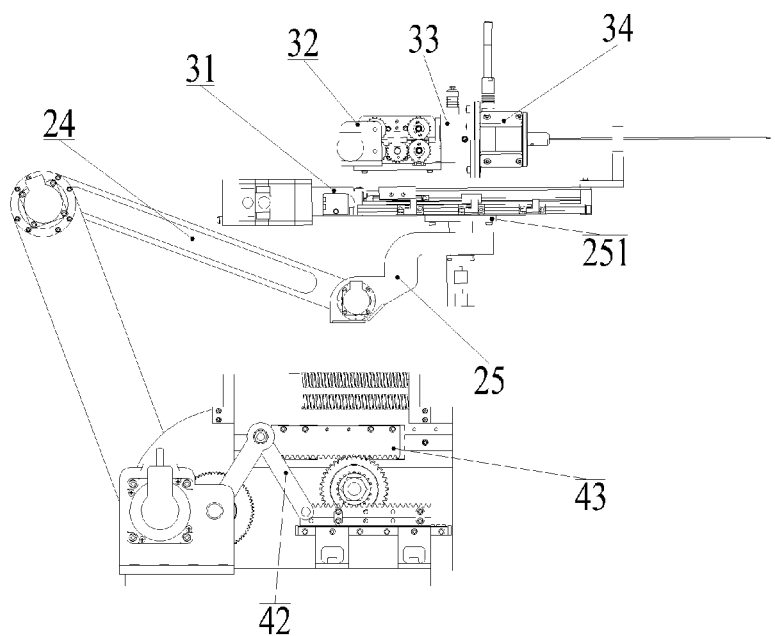
FIG. 2 is a schematic diagram of the front view of the present disclosure.
Figure 3:
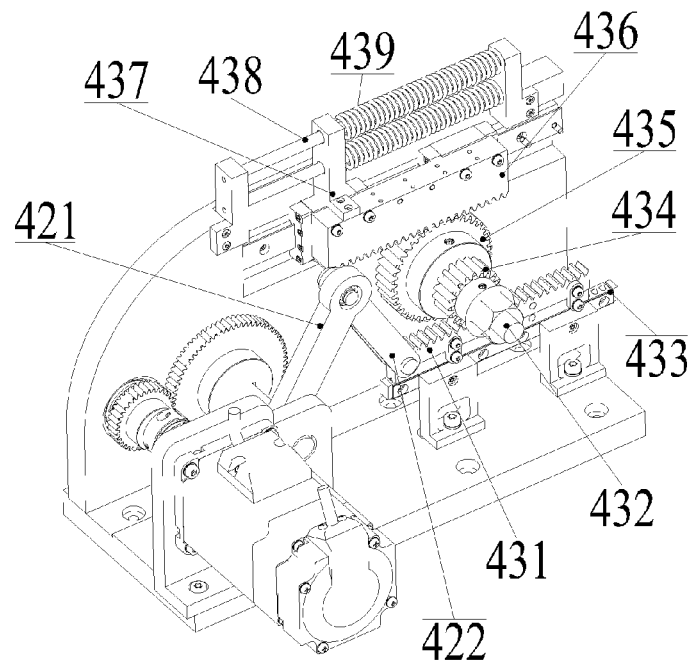
FIG. 3 is a schematic diagram of the three-dimensional structure of the sine elastic amplification torque compensation mechanism of the present disclosure.

In order to make the technical means, creative features, objectives and effects of the present disclosure easy to understand, the present disclosure will be further interpreted below.

As shown in FIGS. 1 to 5, a targeted seed implanting robot suitable for clinical use on a human patient in the lithotomy position includes a rack 1, and also includes:

a position and posture adjustment mechanism 2 provided on the rack 1 to realize transmission of movement and forces under dynamic conditions;

a contact force feedback friction wheel type targeted seed implanting mechanism 3 provided on the position and posture adjustment mechanism 2 to cooperate with a user to improve force information perception ability in the targeted seed implanting process; and a sine elastic amplification moment compensation mechanism 4 provided on the rack 1 and cooperating with the position and posture adjustment mechanism 2 to amplify an elastic force through a sinusoidal force for torque compensation.

The position and posture adjustment mechanism 2 includes a big arm 22, a big arm reduction motor 23 connected with the big arm 22, a driving gear 21 arranged on the big arm 22, a small arm 24 arranged on the big arm 22, a wrist 25 connected with the small arm 24 through a hinge, and a connecting flange 251 connected at the wrist 25.

Using the sine elastic amplification moment compensation mechanism 4 can realize compensation of lower weight moment of any position shape of the big arm 22, reduce fluctuation of driving moment, improve stability of tail-end low-speed operation of the robot, and, based on the position and posture adjusting mechanism, make it possible to adjust an incidence angle of the external pin 342 of the implanting mechanism in a fixed-point mode when it enters into an epidermal incident point, which could plan a pin entrance path more flexibly, and, in addition, the contact force feedback friction wheel type targeted seed implanting mechanism 3 installed at the tail end of the position and posture adjusting mechanism 2 improves the force information perception ability in the targeted seed implanting process.

The contact force feedback friction wheel type targeted seed implanting mechanism 3 includes an external pin driving mechanism 31 and a friction wheel type internal pin driving mechanism 32 which cooperate with the connecting flange 251, a seed loading transition device 33 cooperating with the friction wheel type internal pin driving mechanism 32, and a contact force feedback external pin 34 cooperating with the seed loading transition device 33.

The external pin driving mechanism 31 includes a universal linear sliding table, which performs linear transmission of the external pin 342 by a servo motor driving a screw nut.

The friction wheel type internal pin driving mechanism 32 includes a sliding table 312 arranged on an external pin driving mechanism 31, a bottom plate 321 arranged on the sliding table 312, and two sets of friction wheels 323 distributed left-right symmetrically, the internal pin 322 cooperating with the friction wheels 323 for transmission.

The seed loading transition device 33 is a seed implanting channel 331, the contact force feedback type external pin 34 is a hollow multidimensional force sensor 341, and the external pin 342 and the multidimensional force sensor 341 cooperate for injection.

The friction wheel type internal pin driving mechanism 32 provided on the contact force feedback friction wheel type targeted seed imp-lant implanting mechanism 3 controls rotation direction of the friction wheels 323 to realize reciprocating movement of the internal pin 322 mounted to the friction wheel type internal pin driving mechanism 32, improving compactness of the axial size design.

Figure 4:
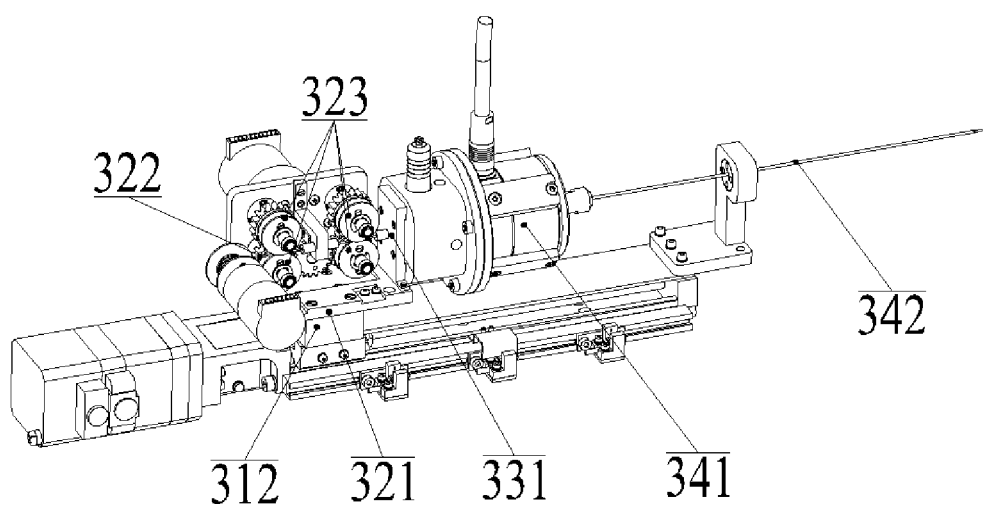
FIG. 4 is a three-dimensional schematic diagram of the contact force feedback friction wheel type targeted seed implant of the present disclosure.
Figure 5:
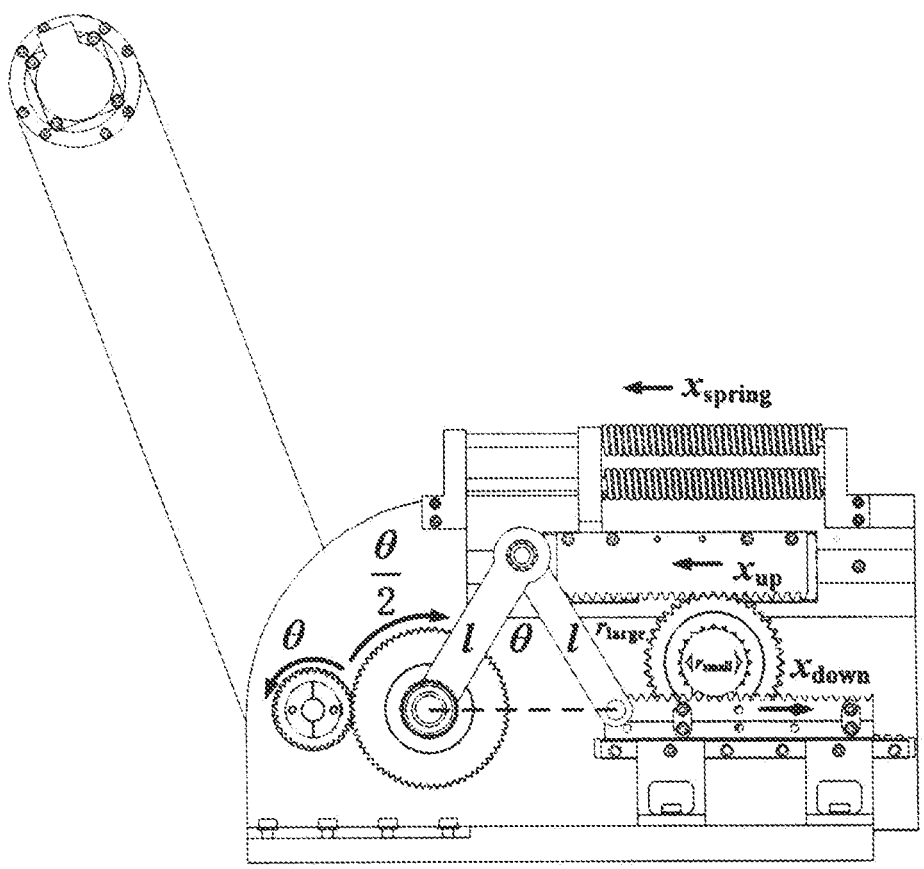

As shown in FIG. 4, several sets of gears that cooperate with each other and the friction wheels 323 are cooperated by a driving motor to control the rotation direction of the friction wheels 323, and the friction wheels 323 rotate and transmit power.

The internal pin 322 is coaxially cooperating with the seed implanting channel 331 of the seed loading transition device 33, and the internal pin 322 reciprocates in and out of the seed implanting channel 331 in a coaxially cooperating manner, so that the seeds can be continuously bombed.

The internal pin 322 and the external pin 342 are installed coaxially. The internal pin 322 can reach the tip of the external pin 342 along the seed implanting channel 331, the hollow multidimensional force sensor 341 and the external pin 342 to push the seeds to the front of the tip of the external pin 342 to achieve placement of the seeds.

The contact force feedback external pin 34 can collect information of multi-dimensional forces and moments in real time when the tip of the external pin 342 contacts soft tissues, and improve the force information perception ability in the targeted seed implanting process.

The sine elastic amplification moment compensation mechanism 4 includes a driven gear 41 meshing with the driving gear 21, a crank slider mechanism 42 that cooperates with the driven gear 41, and an elastic amplification mechanism 43 that cooperates with the crank slider mechanism 42 to achieve elastic force amplification and compensation.

The sine elastic amplification moment compensation mechanism works in the following principle: When the driving gear 21 coaxially mounted on the big arm 22 rotates counterclockwise by an angle of θ, the gear pair with a reduction ratio of 2 to 1 drives the driven gear 41 to rotate clockwise by an angle of θ/2, and the position shape of the crank slider mechanism 42 fixed on the driven gear 41 changes accordingly. At this time, the angle between a crank 421 and a connecting rod 422 on the crank slider mechanism 42 is subject to a change of θ. Meanwhile, a lower sliding gear 431 hinged to a lower end of the connecting rod 422 is driven to move rightwards by a distance of $x_{lower}=2/\sin(\theta/2)$, that is, the length of the crank 421=the length of the connecting rod 422=/, and an upper sliding gear 436 is moved to the left by the elastic amplification mechanism 43 by a distance of $x_{up}=2/\sin(\theta/2)r_2/r_1$, that is, the pinion gear R 434 having a radius of $r_1$, the large gear 435 having a radius of $r_2$, and the two sets of compression springs 439 being compressed with an amount of $x_{spring}=x_{up}$ to the right along a linear guide rod 438. At this time, the reduced gravitational potential energy of the big arm 22 is completely transformed into the increased elastic potential energy of the two sets of compression springs 439; conversely, when the big arm 22 rotates counterclockwise by an angle of θ, the reduced elastic potential energy of the two sets of compression springs 439 is completely transformed into the increased gravitational potential energy for the big arm 22.

The driving gear 21 is connected to the sine elastic amplification moment compensation mechanism 4 through a gear pair. The sine elastic amplification moment compensation mechanism 4 can satisfy compensation for the gravitational moment of the big arm 22, reducing the driving moment fluctuation and power of the big arm reduction motor 23, and improving stability of low-speed movement of the robot.

The crank slider mechanism 42 includes a crank 421 and a connecting rod 422 cooperating with the crank 421; the elastic amplification mechanism 43 includes a lower sliding rack 431 cooperating with the connecting rod 422, a linear slide rail 432 provided on the lower sliding rack 431, a pinion gear 434 meshing with the lower sliding rack 431, a large gear 435 cooperating with the pinion gear 434, an upper sliding rack 436 that cooperates with the large gear 435 through a rack and pinion pair, a slider 437 provided on the upper sliding rack 436, a linear guide rod 438 that cooperates with the slider 437, and several sets of compression springs 439 provided on the linear guide rod 438.

The lower sliding gear 431 meshes with the pinion gear 434 through the rack and pinion pair.

The pinion gear 434 and the large gear 435 cooperate coaxially through a shaft 433.

The large gear 435 is connected to the upper sliding rack 436 through the rack and pinion pair.

The upper sliding rack 436 is fixedly connected with the slider 437.

The slider 437 is mounted on the linear guide rod 438, along which the slider slides left and right.

The two sets of compression springs 439 installed on the linear guide rod 438 are placed between the slider 437 and a right end of the linear guide rod 438.

A method suitable for clinical use of a targeted seed implanting robot on a human patient in the lithotomy position has specific steps as follows:

S1: Driving: driving the big arm reduction motor 23 to cause motion of the driving gear 21 and the big arm 22, respectively;

S2: Meshing: meshing the driving gear 21 with the driven gear 41;

S3: Swing: the driven gear 41, through cooperation with the crank 421, is connected to the connecting rod 422 via a revolute pair, and the driving gear 21 is rotated to cause rotation of the crank 421, the crank 421 causes swing of the connecting rod 422 via the revolute pair, and a distal end of the connecting rod 422 drives the upper sliding rack 436 to move;

S4: Transverse movement: the lower sliding rack 431, when moving horizontally in a transverse direction, drives the upper sliding rack 436 to move horizontally in an opposite direction;

S5: Compensation moment:

a: The upper sliding rack 436 is moved to compresses the several sets of compression springs 439, elastic force of the compression springs 439 being amplified by the pinion gear 434 and the large gear 435 cooperating with the pinion gear 434; and b: The amplified elastic force reacts on the upper sliding rack 436, and moment is transmitted through the big arm 22 and the small arm 24 to the contact force feedback friction wheel type targeted seed implanting mechanism 3;

S6: Linear motion: When the external pin drive mechanism 31 is moving, it drives the external pin 342 to move in a straight line, achieving precise positioning of the external pin 342 by controlling a moving distance of the sliding table 312;

S7: Rotary motion: When the external pin 342 reaches a designated position, the friction wheel type internal pin driving mechanism 32 drives two sets of friction wheels 323 arranged symmetrically to rotate, and the internal pin 322 reciprocating in and out of the seed implanting channel 331 under the action of rolling friction forces provided by the friction wheels 323 and reciprocating into the seed loading transition device 33;

S8: Detection: After entering the hollow multidimensional force sensor 341 fixedly connected to the contact force feedback external pin 34, the hollowed external pin 342 reaches the designated position, and the hollow multidimensional force sensor 341 measures forces and moments received by the external pin 342 in real time when the external pin 342 is moving;

S9: Transmission of information: The force information is transmitted to a controller, which controls motion state of the external pin driving mechanism 31 and the friction wheel type internal pin driving mechanism 32 according to the force information, and performs seed implantation.

The controller in step S9 is an embedded motion controller.

The aforementioned shows and describes the basic principle, main features and advantages of the present disclosure. Those skilled in the art should understand that the present disclosure is not limited by the above-mentioned embodiments. Those depicted in the embodiments and the specification are only principles of the present disclosure. Without departing from the spirit and scope of the present disclosure, the present disclosure shall have various aspects, which all fall into the scope of the present disclosure. The scope of protection claimed by the present disclosure is defined by the appended claims and their equivalents.

What is claimed is:

1. A targeted seed implantation robot suitable for clinical treatment of a human patient in the lithotomy position, comprising:

a rack;

a position and posture adjustment mechanism provided on the rack to realize transmission of movement and forces under dynamic conditions;

a contact force feedback friction wheel type targeted seed implanting mechanism provided on the position and posture adjustment mechanism to cooperate with a user to improve force information perception ability during a targeted seed implanting process; and a sine elastic amplification moment compensation mechanism provided on the rack and cooperating with the position and posture adjustment mechanism to amplify an elastic force through a sinusoidal force for torque compensation.

2. The targeted seed implantation robot according to claim 1, wherein the position and posture adjustment mechanism includes a big arm, a big arm reduction motor connected with the big arm, a driving gear arranged on the big arm, a small arm arranged on the big arm, a wrist connected with the small arm through a hinge, and a connecting flange connected at the wrist.

3. The targeted seed implantation robot according to claim 2, wherein the contact force feedback friction wheel type targeted seed implanting mechanism includes an external pin driving mechanism and a friction wheel type internal pin driving mechanism cooperating with the connecting flange, a seed loading transition device cooperating with the friction wheel type internal pin driving mechanism, and a contact force feedback external pin cooperating with the seed loading transition device.

4. The targeted seed implantation robot according to claim 3, wherein the friction wheel type internal pin driving mechanism includes a sliding table arranged on the external pin driving mechanism, a bottom plate arranged on the sliding table, and two sets of friction wheels distributed left-right symmetrically and cooperating with an internal pin, the internal pin cooperating with the friction wheels for transmission.

5. The targeted seed implantation robot according to claim 3, wherein the seed loading transition device is a seed implanting channel, the contact force feedback type external pin is a hollow multidimensional force sensor, and an external pin and the multidimensional force sensor cooperate for injection.

6. The targeted seed implantation robot according to claim 2, wherein the sine elastic amplification moment compensation mechanism comprises a driven gear meshing with the driving gear, a crank slider mechanism cooperating with the driven gear, and an elastic amplification mechanism that cooperates with the crank slider mechanism to achieve elastic force amplification and compensation.

7. The targeted seed implantation robot according to claim 6, wherein the crank slider mechanism comprises a crank and a connecting rod cooperating with the crank; the elastic amplification mechanism comprises a lower sliding rack cooperating with the connecting rod, a linear slide rail provided on the lower sliding rack, a pinion gear meshing with the lower sliding rack, a large gear cooperating with the pinion gear, an upper sliding rack that cooperates with the large gear through a rack and pinion pair, a slider provided on the upper sliding rack, a linear guide rod that cooperates with the slider, and several sets of compression springs provided on the linear guide rod.

* * * * *